(12) United States Patent
Fosodeder et al.

(10) Patent No.: US 11,457,896 B2
(45) Date of Patent: Oct. 4, 2022

(54) ULTRASOUND IMAGING SYSTEM AND METHOD FOR GENERATING AN ENHANCED IMAGE TO ENHANCE A SHADOW REGION

(71) Applicant: GE Precision Healthcare LLC, Wauwatosa, WI (US)

(72) Inventors: Erwin Fosodeder, Neukirchen an der Vöckla (AT); Gerald Schwarz, Marchtrenk (AT); Carolyn Elizabeth Sweet, Vöcklamarkt (AT)

(73) Assignee: GE Precision Healthcare LLC, Wauwatosa, WI (US)

( * ) Notice: Subject to any disclaimer, the term of this patent is extended or adjusted under 35 U.S.C. 154(b) by 45 days.

(21) Appl. No.: 17/029,956

(22) Filed: Sep. 23, 2020

(65) Prior Publication Data
US 2022/0087650 A1    Mar. 24, 2022

(51) Int. Cl.
*A61B 8/08*    (2006.01)
*A61B 8/00*    (2006.01)
*G01S 15/89*   (2006.01)

(52) U.S. Cl.
CPC .............. *A61B 8/5207* (2013.01); *A61B 8/42* (2013.01); *A61B 8/481* (2013.01); *A61B 8/54* (2013.01); *G01S 15/8979* (2013.01)

(58) Field of Classification Search
CPC .... A61B 8/481; A61B 8/5269; G01S 7/52046
See application file for complete search history.

(56) References Cited

U.S. PATENT DOCUMENTS

| | | | | |
|---|---|---|---|---|
| 5,493,539 A | * | 2/1996 | Haley | G01S 7/539 367/131 |
| 6,108,572 A | * | 8/2000 | Panda | A61B 8/06 600/407 |
| 6,206,833 B1 | | 3/2001 | Christopher | |
| 7,004,905 B2 | | 2/2006 | Christopher | |
| 7,104,956 B1 | | 9/2006 | Christopher | |
| 8,858,442 B2 | * | 10/2014 | Osumi | G06T 5/10 600/443 |
| 9,734,602 B2 | | 8/2017 | Park | |
| 10,687,788 B2 | | 6/2020 | Kang | |
| 2004/0064043 A1 | * | 4/2004 | Rielly | G01S 7/52038 600/437 |
| 2004/0236222 A1 | * | 11/2004 | Mao | G01S 15/8952 600/458 |

(Continued)

*Primary Examiner* — Joel Lamprecht
*Assistant Examiner* — Nyrobi Celestine

(57) ABSTRACT

A method and ultrasound imaging system includes transmitting first ultrasound energy with a first transmit pattern, receiving first ultrasound data based on the first ultrasound energy, and generating a first image based on the first ultrasound data. The method and system includes entering a shadow reduction mode and performing the following steps in the shadow reduction mode: transmitting second ultrasound energy with a second transmit pattern configured to have greater penetration than the first transmit pattern, receiving second ultrasound data based on the second ultrasound energy, generating a mask identifying a shadow region and generating an enhanced image including an enhanced shadow region, wherein the second ultrasound data is used to generate the enhanced shadow region, and displaying the enhanced image.

13 Claims, 7 Drawing Sheets

(56) References Cited

U.S. PATENT DOCUMENTS

| | | | |
|---|---|---|---|
| 2008/0232718 A1* | 9/2008 | Avinash | A61B 6/563 |
| | | | 382/305 |
| 2011/0160586 A1* | 6/2011 | Li | G01S 15/8952 |
| | | | 600/443 |
| 2014/0243667 A1* | 8/2014 | Wilkening | A61B 8/58 |
| | | | 600/438 |
| 2016/0089116 A1* | 3/2016 | Duncan | A61B 8/5207 |
| | | | 600/440 |
| 2019/0162831 A1* | 5/2019 | Berlin | A61B 8/4483 |
| 2020/0187911 A1* | 6/2020 | Park | A61B 8/587 |

* cited by examiner

ULTRASOUND IMAGING SYSTEM AND METHOD FOR GENERATING AN ENHANCED IMAGE TO ENHANCE A SHADOW REGION

FIELD OF THE INVENTION

This disclosure relates generally to an ultrasound imaging system and a method for generating and displaying an enhanced image including an enhanced shadow region.

BACKGROUND OF THE INVENTION

Ultrasound imaging is an imaging modality based on echoes received from transmitted ultrasound energy. Ultrasound imaging has many clinical uses including general imaging, cardiac imaging, musculoskeletal imaging (MSK), point-of-care, primary care, and obstetrics/women's health. Ultrasound imaging has many advantages as an imaging modality. The ultrasound energy used to acquire images is non-ionizing and therefore safer for many applications than other imaging modalities that rely on X-ray or other ionizing forms of radiation. Additionally, ultrasound imaging is a relatively affordable imaging modality, which makes it well-suited for widespread use in a variety of clinical scenarios.

In ultrasound imaging, image quality is typically related to a signal-to-noise ratio (SNR) of the ultrasound data. As a general rule, a higher signal-to-noise ratio will result in better image quality compared to a lower signal-to-noise ratio. One technique that conventional ultrasound imaging systems use to improve the signal-to-noise ratio is to use various forms of compound imaging. For example, many conventional ultrasound imaging systems will use a form of frequency compounding to generate images with improved signal-to-noise ratios. However, the frequency compounding is typically optimized to provide good resolution, which tends to include emphasizing higher frequencies more than lower frequencies when performing the frequency compounding.

One problem with using higher frequencies or predominantly higher frequencies to generate ultrasound images is that while higher frequencies of ultrasound have higher resolution, they do not penetrate as well as lower frequencies. Imaging with higher frequencies can result in the generation of images with a shadow region. The shadow region is an area or areas in an image with either a very low intensity signal or zero signal. The shadow region may be caused by, for example, dense structures such as bone that block the ultrasound energy and/or the shadow region may also be the result of an edge-refraction shadow. The shadow region is typically represented by one or more dark areas on the displayed ultrasound image. A shadow region in an image may make it difficult or impossible for a clinician to accurately understand the patient's anatomy and/or make proper measurements based on an image using conventional ultrasound imaging techniques.

For at least the reasons described above, there is a need for an improved ultrasound imaging system and method for generating an enhanced image with an enhanced shadow region.

BRIEF DESCRIPTION OF THE INVENTION

The above-mentioned shortcomings, disadvantages and problems are addressed herein which will be understood by reading and understanding the following specification.

In an embodiment, a method of ultrasound imaging includes transmitting first ultrasound energy from an ultrasound probe with a first transmit pattern, receiving first ultrasound data based on the first ultrasound energy, generating a first image based on the first ultrasound data, and entering a shadow-reduction mode in response to a user input after said generating the first image. The method includes performing the following steps while in the shadow-reduction mode: transmitting second ultrasound energy from the ultrasound probe with a second transmit pattern that is configured to have a greater penetration than the first transmit pattern; receiving second ultrasound data based on the second ultrasound energy; generating a mask identifying a shadow region; generating an enhanced image including a non-shadow region and an enhanced shadow region, wherein the second ultrasound data is used to generate the enhanced shadow region in the enhanced image based on the shadow region in the mask; and displaying the enhanced image on a display device.

In an embodiment, an ultrasound imaging system includes a display device, an ultrasound probe and a processor in electronic communication with both the display device and the ultrasound probe. The processor is configured to control the ultrasound probe to transmit first ultrasound energy with a first transmit pattern, receive first ultrasound data based on the first ultrasound energy, and generate a first image based on the first ultrasound data. The processor is configured to enter a shadow-reduction mode in response to a user input after generating the first image. The processor is configured to perform the following steps while in the shadow-reduction mode: control the ultrasound probe to transmit second ultrasound energy with a second transmit pattern that is configured to have greater penetration than the first transmit pattern; receive second ultrasound data based on the second ultrasound energy; generate a mask identifying a shadow region; generate an enhanced image including a non-shadow region and an enhanced shadow region, wherein the second ultrasound data is used to generate the enhanced shadow region in the enhanced image based on the shadow region in the mask, and display the enhanced image on the display device.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
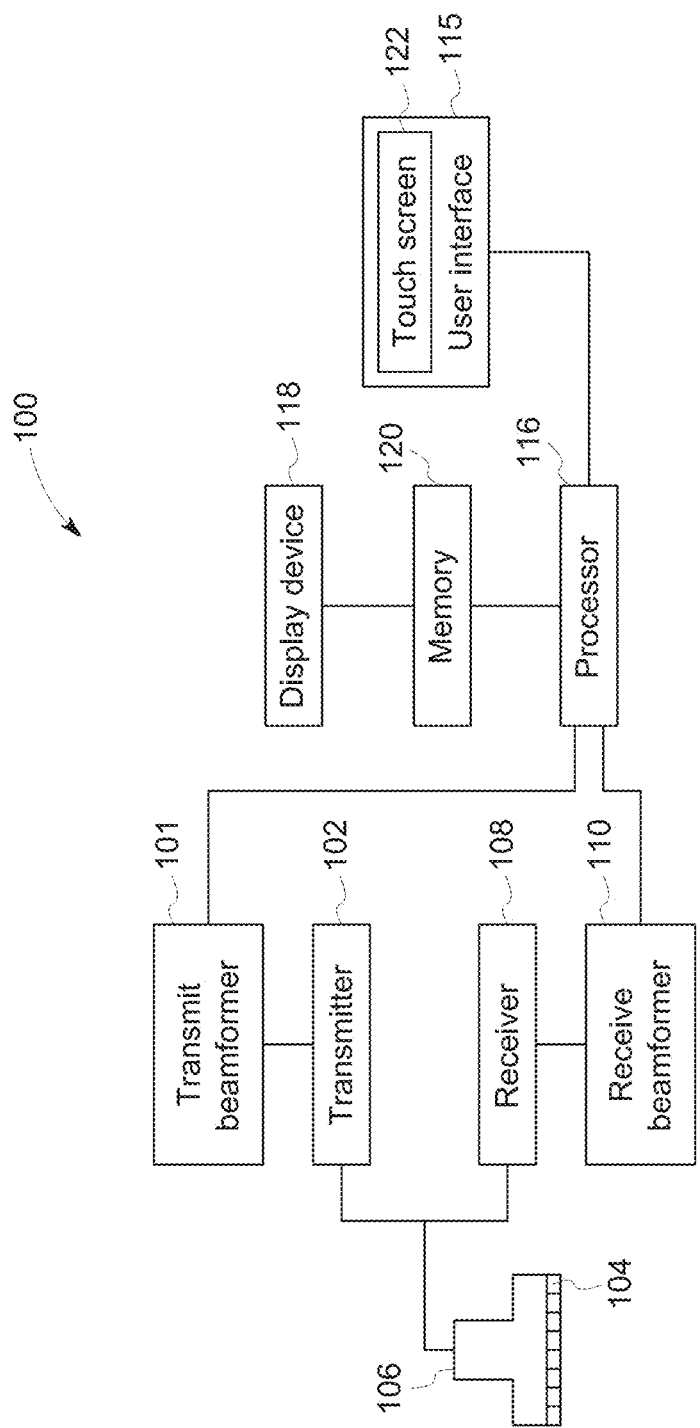
FIG. 1 is a schematic diagram of an ultrasound imaging system in accordance with an embodiment.

FIG. 1 is a schematic diagram of an ultrasound imaging system 100 in accordance with an embodiment. The ultrasound imaging system 100 includes a transmit beamformer 101 and a transmitter 102 that drive elements 104 within an ultrasound probe 106 to emit pulsed ultrasonic signals into a body (not shown). The ultrasound probe 106 may be any type of probe, including a linear probe, a curved array probe, a 1.25D array probe, a 1.5D array probe, a 1.75D array probe, or 2D array probe according to various embodiments. The ultrasound probe 106 may also be a mechanical probe, such as a mechanical 4D probe or a hybrid probe according to other embodiments. The ultrasound probe 106 may be used to acquire ultrasound data that contains information about a region or a volume within a patient. Still referring to FIG. 1, the pulsed ultrasonic signals are back-scattered from structures in the body, like blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data. According to some embodiments, the ultrasound probe 106 may contain electronic circuitry to do all or part of the transmit beamforming and/or the receive beamforming. For example, all or part of the transmit beamformer 101, the transmitter 102, the receiver 108 and the receive beamformer 110 may be situated within the ultrasound probe 106. The terms "scan" or "scanning" may also be used in this disclosure to refer to acquiring data through the process of transmitting and receiving ultrasonic signals. The terms "data" and "ultrasound data" may be used in this disclosure to refer to either one or more datasets acquired with an ultrasound imaging system. A user interface 115 may be used to control operation of the ultrasound imaging system 100. The user interface 115 may be used to control the input of patient data, or to select various modes, operations, and parameters, and the like. The user interface 115 may include a one or more user input devices including a keyboard, hard keys, a touch pad, a track ball, one or more rotary controls, one or more sliders, soft keys, or any other user input devices. The user interface 115 may include a touch screen such as the touch screen 122 shown in the embodiment of FIG. 1. The touch screen 122 is configured to receive touch and/or multi-touch inputs from a user. The processor 116 is configured to convert touch inputs received at the touch screen 122 into operational commands. The touch screen 122 may be configured to display at least one of an image and a graphical user interface. According to an embodiment, the touch screen 122 may be positioned so it is easier to reach for a user. For example, the angle and the height of the touch screen 122 may be different than the display device 118. According to some embodiments, the touch screen 122 may be configured to show an image in addition to or in place of a graphical user interface. For example, the touch screen 122 may be configured to display a version of the image displayed on the display device 118. According to some embodiments, the image displayed on the touch screen 122 may be a smaller version of the image displayed on the main display 118. Other embodiments may not include a touch screen as part of the user interface. In some embodiments, the display device 118 may be a touch-sensitive display device. For example, the display device may include a touch-sensitive surface and the display device 118 may function as a user input device configured to receive one or more of single-touch inputs, multi-touch inputs, and/or gestures. In some embodiments, the ultrasound imaging system 100 may include both the touch screen 122 and a touch-sensitive display device.

The ultrasound imaging system 100 also includes a processor 116 to control the transmit beamformer 101, the transmitter 102, the receiver 108 and the receive beamformer 110. The receive beamformer 110 may be either a conventional hardware beamformer or a software beamformer according to various embodiments. If the receive beamformer 110 is a software beamformer, it may comprise one or more of the following components: a graphics processing unit (GPU), a microprocessor, a central processing unit (CPU), a digital signal processor (DSP), or any other type of processor capable of performing logical operations. The receive beamformer 110 may be configured to perform conventional beamforming techniques as well as techniques such as retrospective transmit beamforming (RTB).

The processor 116 is in electronic communication with the ultrasound probe 106. The processor 116 may control the ultrasound probe 106 to acquire ultrasound data. The processor 116 controls which of the elements 104 are active and the shape of a beam emitted from the ultrasound probe 106. The processor 116 is also in electronic communication with the display device 118, and the processor 116 may process the ultrasound data into images for display on the display device 118. For purposes of this disclosure, the term "electronic communication" is defined to include both wired and wireless connections. The processor 116 may include a central processing unit (CPU) according to an embodiment. According to other embodiments, the processor 116 may include other electronic components capable of carrying out processing functions, such as a digital signal processor, a field-programmable gate array (FPGA), a graphics processing unit (GPU) or any other type of processor. According to other embodiments, the processor 116 may include multiple electronic components capable of carrying out processing functions. For example, the processor 116 may include two or more electronic components selected from a list of electronic components including: a central processing unit (CPU), a digital signal processor (DSP), a field-programmable gate array (FPGA), and a graphics processing unit (GPU). According to another embodiment, the processor 116 may also include a complex demodulator (not shown) that demodulates the RF data and generates raw data. In another embodiment the demodulation can be carried out earlier in the processing chain. The processor 116 may be adapted to perform one or more processing operations according to a plurality of selectable ultrasound modalities on the data. The data may be processed in real-time during a scanning session as the echo signals are received. For the purposes of this disclosure, the term "real-time" is defined to include a procedure that is performed without any intentional delay. Real-time frame or volume rates may vary based on the size of the region or volume from which data is acquired and the specific parameters used during the acquisition. The data may be stored temporarily in a buffer (not shown) during a scanning session and processed in less than real-time in a live or off-line operation. Some embodiments of the invention may include multiple processors (not shown) to handle the processing tasks. For example, a first processor may be utilized to demodulate and decimate the RF signal while a second processor may be used to further process the data prior to display as an image. It should be appreciated that other embodiments may use a different arrangement of processors. For embodiments where the receive beamformer 110 is a software beamformer, the processing functions attributed to the processor 116 and the software beamformer hereinabove may be performed by a single processor such as the receive beamformer 110 or the processor 116. Or, the processing functions attributed to the processor 116 and the software beamformer may be allocated in a different manner between any number of separate processing components.

According to an embodiment, the ultrasound imaging system 100 may continuously acquire ultrasound data at a frame-rate of, for example, 10 Hz to 30 Hz. Images generated from the data may be refreshed at a similar frame-rate. Other embodiments may acquire and display data at different rates. For example, some embodiments may acquire ultrasound data at a frame rate of less than 10 Hz or greater than 30 Hz depending on the size of the volume and the intended application. For example, many applications involve acquiring ultrasound data at a frame rate of 50 Hz or more. A memory 120 is included for storing processed frames of acquired data. In an exemplary embodiment, the memory 120 is of sufficient capacity to store frames of ultrasound data acquired over a period of time at least several seconds in length. The frames of data are stored in a manner to facilitate retrieval thereof according to its order or time of acquisition. The memory 120 may comprise any known data storage medium.

Optionally, embodiments of the present invention may be implemented utilizing contrast agents. Contrast imaging generates enhanced images of anatomical structures and blood flow in a body when using ultrasound contrast agents including microbubbles. After acquiring data while using a contrast agent, the image analysis includes separating harmonic and linear components, enhancing the harmonic component and generating an ultrasound image by utilizing the enhanced harmonic component. Separation of harmonic components from the received signals is performed using suitable filters. The use of contrast agents for ultrasound imaging is well-known by those skilled in the art and will therefore not be described in further detail.

In various embodiments of the present invention, data may be processed by other or different mode-related modules by the processor 116 (e.g., B-mode, Color Doppler, M-mode, Color M-mode, spectral Doppler, Elastography, TVI, strain, strain rate, and the like) to form 2D or 3D images or data. For example, one or more modules may generate B-mode, color Doppler, M-mode, color M-mode, spectral Doppler, Elastography, TVI, strain, strain rate and combinations thereof, and the like. The image beams and/or frames are stored and timing information indicating a time at which the data was acquired in memory may be recorded.

The processor 116 is configured to perform scan conversion operations to convert the image frames from coordinates beam space to display space coordinates. The processor 116 may be configured to read the image frames from a memory and display the image frames in real time while a procedure is being carried out on a patient. The processor 116 may store the image frames in an image memory, from which the images are read and displayed. The ultrasound imaging system 100 may be a console-based system, a laptop, a handheld or hand-carried system, or any other configuration.

According to various embodiments, the ultrasound probe 106 may be configured to be in electronic communication with other components of the ultrasound imaging system 100 such as the processor 116, the receiver 108, the receive beamformer 110, the transmitter 102, and the transmit beamformer 101 through either wired or wireless techniques. For example, according to an embodiment, the ultrasound probe 106 may be battery-powered and configured to receive instructions from the processor 116 and transmit data to the processor 116 over one or more wireless communication channels.

The various methods and processes, such as those described hereinbelow with respect to FIG. 2, can be stored as executable instructions in a non-transitory computer-readable medium, such as the memory 120, in the ultrasound imaging system 100 or in the processor 116. In another embodiment, processor 116 may include the instructions stored in a non-transitory computer-readable medium, and may apply the methods described herein. In yet another embodiment, the methods and processes described herein may be distributed across the memory 120 and the processor 116.

Figure 2:
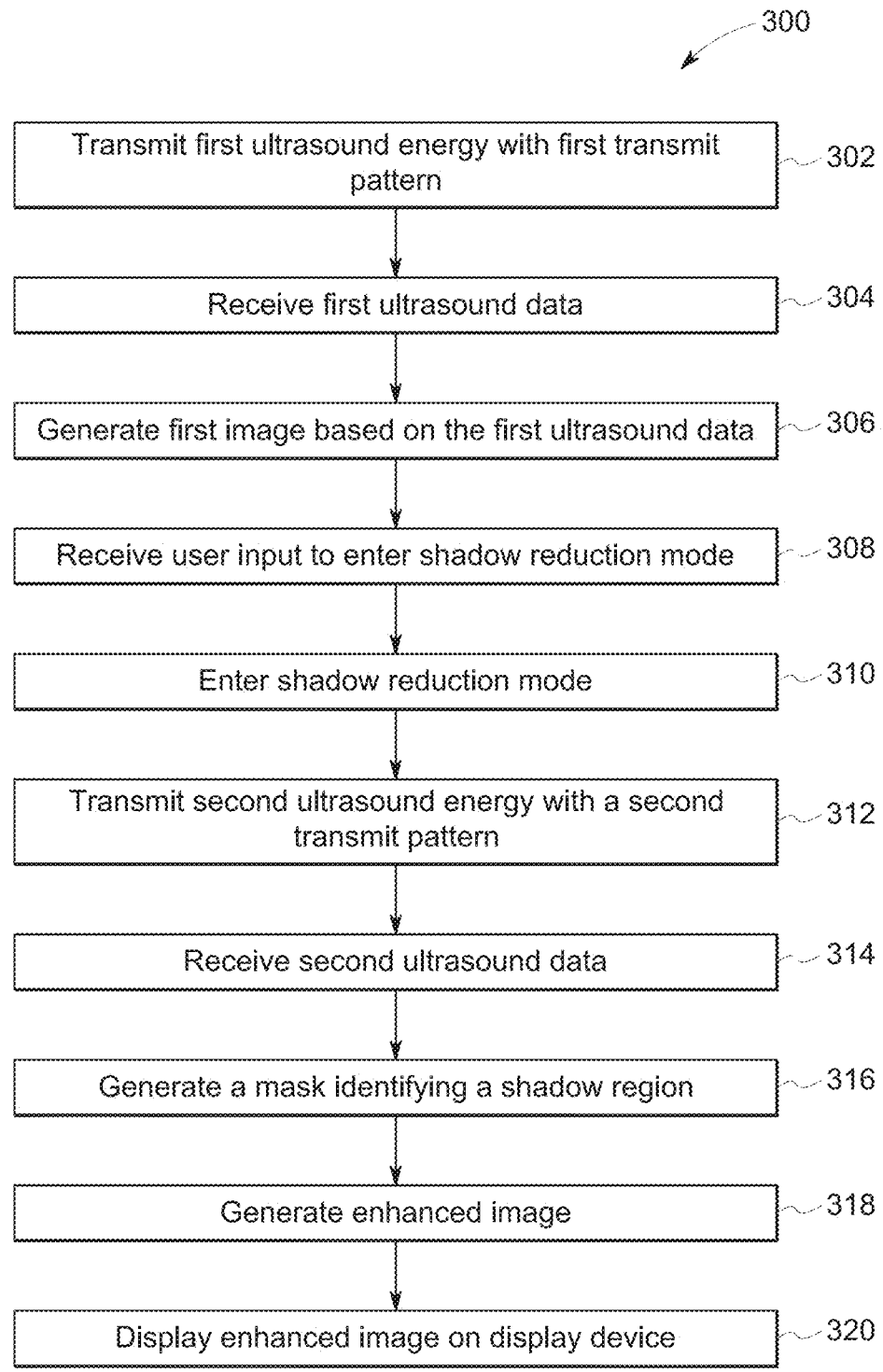
FIG. 2 is a flow chart of a method in accordance with an embodiment.

FIG. 2 is a flow chart of a method 300 in accordance with an exemplary embodiment. The individual blocks of the flow chart represent steps that may be performed in accordance with the method 300. Additional embodiments may perform the steps shown in a different sequence and/or additional embodiments may include additional steps not shown in FIG. 2. The technical effect of the method 300 is the generation and display of an enhanced image with an enhanced shadow region on the display device 118. The method 300 will be described in accordance with an exemplary embodiment where the method 300 is performed by the ultrasound imaging system 100 shown in FIG. 1.

At step 302, the processor 116 controls the ultrasound probe 106 to transmit first ultrasound energy using a first transmit pattern. The processor 116 controls the transmit beamformer 101 and the transmitter 102 to transmit the first ultrasound energy from the ultrasound probe 106 using the first transmit pattern. The first transmit pattern includes the specific parameters used during transmission of the first ultrasound energy. For example, the first transmit pattern includes a center frequency of the transmitted first ultrasound energy and a bandwidth of the transmitted first ultrasound energy. Additionally, different transmit patterns may be used for different imaging modes. For example, first transmit pattern may include a pulse inversion for harmonic imaging. According to other embodiments, the first transmit pattern may not include pulse inversion. The processor 116 may be able to control other parameters of the first transmit pattern, such as intensity according to various embodiments.

According to an embodiment, first transmit pattern may be a run-length encoded (RLE) transmit pattern. The RLE transmit pattern may be configured/optimized to, for example, generate spectra targets around one or more frequencies. The RLE transmit pattern may be used to generate an apodization of a transmit aperture associated with the first transmit pattern. The RLE transmit pattern may be used to improve one or both of axial and lateral resolution in the first ultrasound data.

According to an embodiment, the first transmit pattern may include the use of a linear pulser in order to reduce unwanted frequency components, such as harmonics. The linear pulse may help to minimize image quality degradation of the first image in addition to reducing heating of the ultrasound probe 106.

According to another embodiment, the first transmit pattern may include a pulse inversion technique including both a normal waveform and an inverted waveform. Pulse inversion is typically used during harmonic imaging. The processor 116 controls the probe 106 to transmit a normal waveform T1 and an inverted waveform T2. Then, processor 116 receives a first received signal $S1_1$ from the normal waveform and a second received signal $S2_1$ from the inverted waveform. The first received signal $S1_1$ and the second received signal $S2_1$ are summed according to Equation 1 (shown below) to generate the pulse inversion signal (Phi):

$$PI_1 = S1_1 + S2_1 \qquad \text{Equation 1}$$

The operation of $PI_1 = S1_1 + S2_1$ cancels the fundamental portions of the signal due and $PI_1$ is the $2^{nd}$ harmonic.

At step 304, the processor 116 receives first ultrasound data. According to an embodiment, the ultrasound probe 106 receives echoes from the imaged tissue based on the first ultrasound energy that was transmitted during step 302. Referring to FIG. 1, the echoes are received by the elements 104 of the ultrasound probe 106. The elements 104 convert the acoustic waves into electrical signals which then pass to the receiver 108 and the receive beamformer 110. As described hereinabove, the receive beamformer 110 applies beamforming delays to the electrical signals to generate first ultrasound data. The term "ultrasound data" may be used to refer to data from the elements 104 at various positions in a receive processing chain. For example, "ultrasound data" may be used to refer to the electrical signals generated from the elements 104 in response to receiving the echoes, which is also known as "raw data"; "ultrasound data" may refer to the echoes that have been beamformed by the receive beamformer 110, which is also known as "beamformed data"; and "ultrasound data" may be used to refer to scan-converted data that has been scan-converted by the processor 116 and is ready for display on the display device 118. According to an embodiment the processor 116 may process the ultrasound data into two or more different components with different frequencies. For example, the processor 116 may decompose the ultrasound data into a high-frequency component and a low-frequency component using a technique such as Fourier processing.

Next, at step 306, the processor 116 generates a first image based on the first ultrasound data. According to an embodiment, the first image may not be scan-converted. According to other embodiments, the first image may be scan-converted and ready for display on the display device 118.

According to an embodiment, the processor 116 may generate the first image using frequency compounding. For example, the processor 116 may decompose the first ultrasound data into a high-frequency component and a low-frequency component. A lower frequency image may be generated based on the low-frequency component and a higher frequency image may be generated based on the high-frequency component. Then, the processor 116 may compound the lower frequency image with the higher frequency image to generate a frequency-compounded image based on the first ultrasound data. Frequency compounding typically results in images with lower amounts of speckle compared to images that have not been frequency compounded.

At step 308, the processor 116 receives a user input to enter a shadow-reduction mode. According to exemplary embodiments, the user input may be entered through the touch screen 122 or by selecting a dedicated hard key or button. According to an embodiment, the user input may be entered using a touch-sensitive display, a mouse, a touch pad or a trackball in order to interface with a graphical user interface (GUI) displayed on the display device 118 or the touch screen 122. At step 310, the processor 116 enters a shadow reduction mode in response to receiving the user input at step 308.

Once in the shadow reduction mode at step 312, the processor 116 controls the ultrasound probe 106, the transmitter 102 and the transmit beamformer 101 to transmit second ultrasound energy using a second transmit pattern that is configured to have greater penetration than the first transmit pattern used during the transmission of the first ultrasound energy at step 302. The second transmit pattern may be adjusted in various ways with respect to the first transmit pattern in order to gain greater penetration.

According to an embodiment, the second transmit pattern may be a coded excitation technique. Coded excitation involves the transmission of long-coded waveforms and correlating the long-coded waveforms used during transmission with the received signals. Coded excitation is commonly used in radar, but its use for ultrasound imaging is still relatively new. Using a second transmit pattern that is a coded excitation may be used to increase the signal-to-noise ratio or to increase penetration depth. When tuned for increased penetration, coded excitation typically results in side-lobe artifacts that are undesirable for most general imaging purposes. According to an embodiment, the coded excitation transmit patterns may be a time-coded coded excitation pattern.

One way to gain additional penetration is for the second transmit pattern to be at a lower frequency than the first transmit pattern. Lower frequency ultrasound has increased penetration at the expense of resolution compared to higher frequency ultrasound. The second ultrasound energy may, for instance, be transmitted with a second transmit pattern that has a lower center frequency than the first transmit pattern used to transmit the first ultrasound energy. According to one embodiment, the second transmit pattern may have a lower center frequency than the first transmit pattern. For example, the first transmit pattern used to transmit the first ultrasound energy may have a first center frequency and the second transmit pattern used to transmit the second ultrasound energy may have a second center frequency that is lower than the first transmit pattern. The lower center frequency of the second transmit pattern will provide improved penetration compared to the first transmit pattern.

According to an embodiment, it may be desirable to have the center frequency of the second transmit pattern at least 5% lower than the center frequency of the first transmit pattern. According to an embodiment, it may be desirable to have the center frequency of the second transmit pattern at least 10% lower than the center frequency of the first transmit pattern. According to other embodiments, it may desirable to have the center frequency of the second transmit pattern at least 20% lower than the center frequency of the first transmit pattern in order to provide a greater improvement in penetration depth. According to an embodiment, the first transmit pattern may have a center frequency of 5 MHz and the second transmit pattern may have a center frequency of 4.5 MHz. It should be appreciated by those skilled in the art that other frequencies may be used for the first transmit pattern and the second transmit pattern according to various embodiments.

According to an embodiment, the second transmit pattern may be a pulse inversion transmit pattern that is configured to have increased penetration compared to the first transmit pattern. For example, the second transmit pattern may be described by Equation 2, shown below:

$$PI_2 = (S1_2 * W1) + (S2_2 * W2) \qquad \text{Equation 2}$$

Where $PI_2$ is pulse inverted ultrasound data; $S1_2$ is the received signal from the normal waveform; W1 is the weight applied to the received signal from the normal waveform $S1_2$; $S2_2$ is the received signal from the inverted waveform; and W2 is the weight applied to the received signal from the inverted waveform $S2_2$. According to an embodiment, the first ultrasound data may be acquired using the first transmit pattern described by Equation 1 and the second ultrasound data may be acquired using the second transmit pattern described by Equation 2. If the weights W1 and W2 in Equation 2 are both set to a value of "1", Equation 2 will be the same as Equation 1. Using Equation 1 may be desirable for imaging in normal non-shadow areas. However, in order to gain additional penetration, such as in a shadow region like the shadow region 402, the processor 116 may implement Equation 2 where one or both of W1 and W2 are set to values other than "1".

For example, the processor 116 may adjusts the values of W1 and W2 so that the weight applied to $S1_2$ and $S2_2$ are variable over depth. If $S1_2$ and $S2_2$ correlate well with each other, the processor 116 may be configured to use a value of "1" or close to "1" for W1 and W2. However, the processor 116 may use a value of less than "1" for either W1 or W2 in order to increase the penetration, at the expense of signal-to-noise ratio, of the second transmit pattern. According to various embodiment, the processor 116 may use values between 1 and −1 for either W1 or W2.

According to another embodiment, the processor 116 may use run-length encoded (RLE) transmit pattern for the second transmit pattern. The RLE pattern may be configured to provide greater penetration than the first transmit pattern. According to another embodiment, the processor 116 may use a second transmit pattern that includes a linear pulser. The second transmit pattern including the linear pulse may be configured to provide greater penetration than the first transmit pattern. The processor 116 may adjust other parameters of the second transmit pattern to provide greater penetration than the first transmit pattern. For example, the processor 116 may set a transmit focus to a deeper depth in the second transmit pattern compared to the first transmit pattern in order to provide greater penetration. The processor 116 may configure the second transmit pattern to have a larger transmit aperture in the second transmit pattern than in the first transmit pattern to increase the penetration of the second transmit pattern. The processor 116 may reduce the bandwidth of the second transmit pattern compared to the first transmit pattern in order to increase the energy and provide greater penetration of the second transmit pattern compared to the first transmit pattern. The processor 116 may also use frequency focus compounding (FFC). Additionally, the processor 116 may combine two or more of the techniques described hereinabove to increase the penetration of the second transmit pattern. For example, the processor 116 may use a combination of two or more of setting a transmit focus to a deeper depth, using a transmit pattern with a larger transmit aperture, reducing the bandwidth of the second transmit pattern, and using frequency focus compounding to provide a second transmit pattern with greater penetration than the first transmit pattern.

At step 314 of the method 300, the processor 116 receives second ultrasound data. According to an embodiment, the ultrasound probe 106 receives echoes from the imaged tissue based on the second ultrasound energy that was transmitted during step 312. Referring to FIG. 1, the echoes are received by the elements 104 of the probe 106. The elements 104 convert the acoustic waves into electrical signals which then pass to the receiver 108 and the receive beamformer 110. As described hereinabove, the receive beamformer 110 applies beamforming delays to the electrical signals to generate second ultrasound data.

At step 316, the processor 116 generates a mask based on either the first ultrasound data or the second ultrasound data. According to a first embodiment, the processor 116 may generate the mask based on the first ultrasound data. For example, the processor 116 may generate the mask based on the first ultrasound data after it has been beamformed by the receive beamformer 110, but before it has been scan-converted for display on the display device 118. For purposes of this disclosure, we may refer to ultrasound data as an "image" after it has been beamformed. According to other embodiments, the processor 116 may generate the mask based on the first ultrasound data after it has been scan-converted and is ready for display as an image on the display device 118.

According to a second embodiment, the processor 116 may generate the mask based on the second ultrasound data. The processor 116 may generate the mask based on the second ultrasound data after it has been beamformed by the receive beamformer 110, but before it has been scan-converted for display on the display device 118. According to other embodiments, the processor 116 may generate the mask based on the second ultrasound data after it has been scan-converted and is ready for display as an image on the display device 118.

Figure 3:
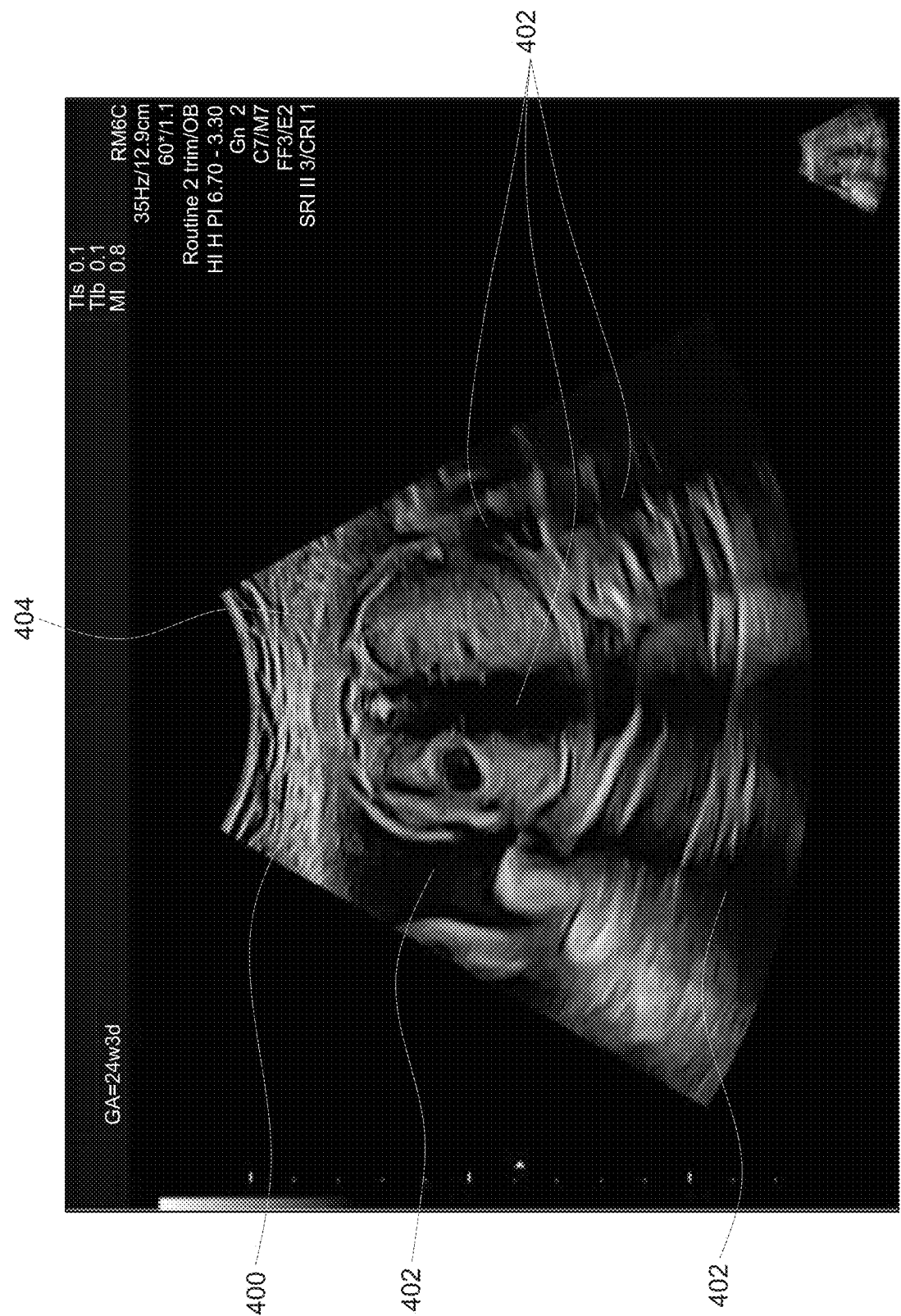
FIG. 3 is an image in accordance with an embodiment.

The processor 116 is configured to identify a shadow region based on either the first ultrasound data or the second ultrasound data. The shadow region may be a single connected region or a plurality of separate shadow subregions. The shadow region is the portion of an ultrasound image where the data lacks enough intensity to generate a diagnostically useful image. FIG. 3 shows an image 400 generated based on ultrasound data. In the example shown in FIG. 3, the image 400 has been scan-converted since it is in a displayable format. As discussed hereinabove, the processor 116 may be configured to generate the mask based on an image that has not been scan-converted as well. The image 400 includes a shadow region 402, which in the example shown on FIG. 3, includes a plurality of disconnected shadow subregions. In other embodiments, the shadow region may be a single connected region. The shadow region 402 is represented on the image 400 as dark regions because either the ultrasound data acquired from the shadow region 402 has too low of an intensity to be represented as a lighter greyscale value on the image 400 or because there is no information acquired from the anatomical regions corresponding to the shadow region 402. The shadow region 402 may be caused by one or more acoustically dense structures that are occluding, or shadowing, anatomical structures that are deeper than the acoustically dense structure or structures. For example, ultrasound energy does not pass through dense structures such as bone. It is common to have shadow regions caused by bones when imaging structure at a greater depth than the bones. When imaging a patient in a prone position with the spine in an anterior position, it is common for ultrasound images to include shadow regions from the spine and/or ribs. Rib shadows are also a common problem during ultrasound examinations of lungs or the thorax of a patient from an external probe position. Acoustically dense structures can also cause an edge refraction shadow at positions that are not directly obscured by the dense structure. Edge refraction shadows are a problem when imaging areas adjacent to an acoustically dense structure such as a bone. Shadow regions in images generated based on ultrasound data may result in a reduction of image quality and/or make it difficult or impossible to obtain accurate measurements based on the image.

Referring back to step 316, the processor 116 may be configured to identify the shadow region in the image based on either the first ultrasound data or the second ultrasound data based on an intensity threshold. For example, the processor 116 may identify the shadow region 402 by identifying the portion of the image 400 with an intensity below an intensity threshold. The processor 116 may use a predetermined intensity threshold or the processor 116 may be configured set the intensity threshold based on the intensity data in the image 400. The processor 116 may set the threshold based on the average intensity of the image 400. For example, the processor 116 may set the intensity threshold as a specified percentage of the average intensity of the image 400. According to other embodiments, the threshold intensity may be user configurable or automatically adjusted based on parameter settings used during the acquisition of the data. For example, according to an embodiment, a change of transmit power may result in the processor 116 automatically adjusting the threshold used for the generation of the mask. Transmit power is just one example of a parameter setting. The processor 116 may automatically adjust the threshold used for the generation of the mask according to any parameter used when either transmitting ultrasound energy or receiving ultrasound data. For example, the processor 116 may be configured to automatically adjust the threshold used for the generation of the mask based on parameters such as focus depth, transmission frequency, line spacing, etc.

Figure 4:
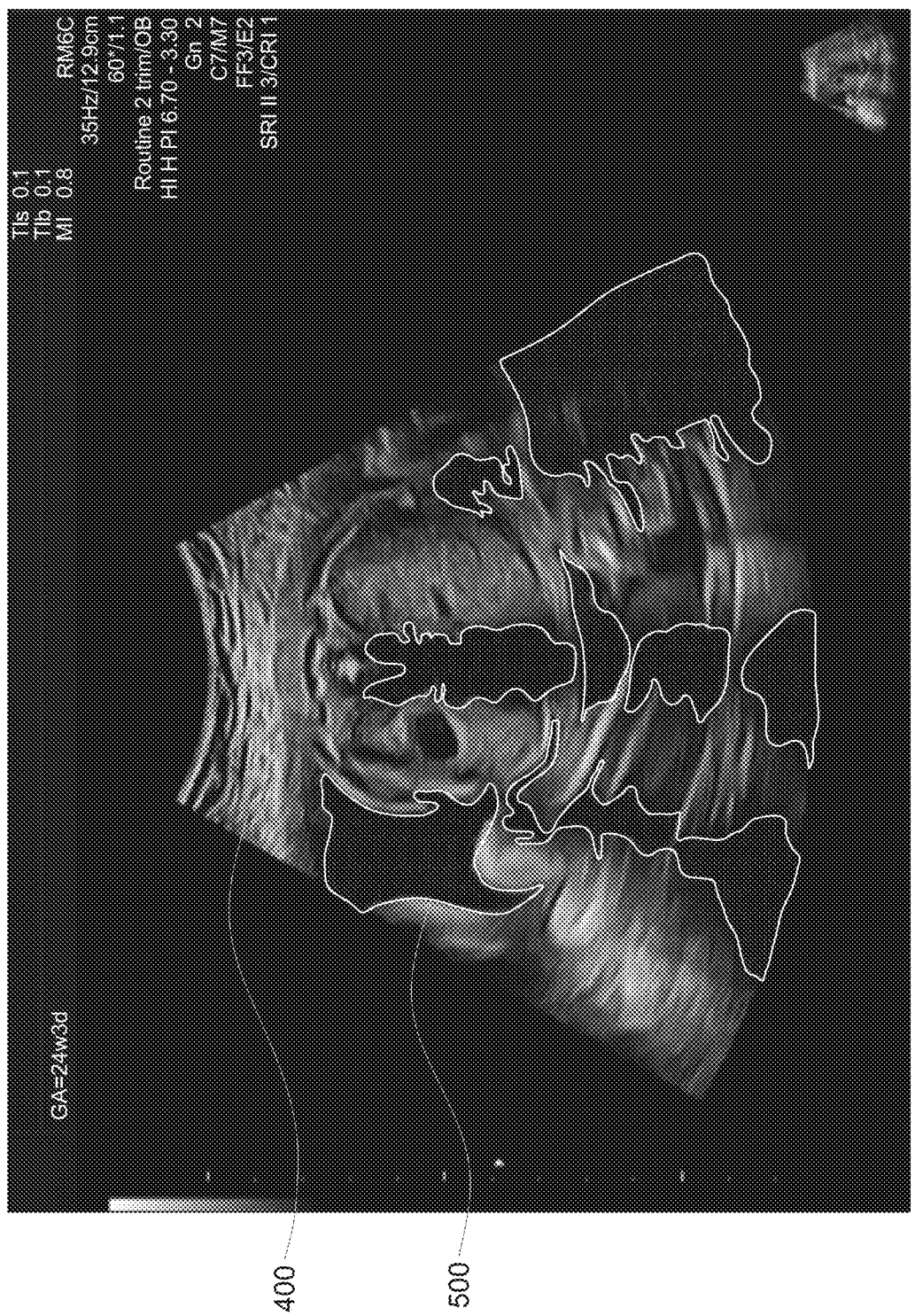
FIG. 4 is a representation of a mask superimposed on an image in accordance with an embodiment.
Figure 5:
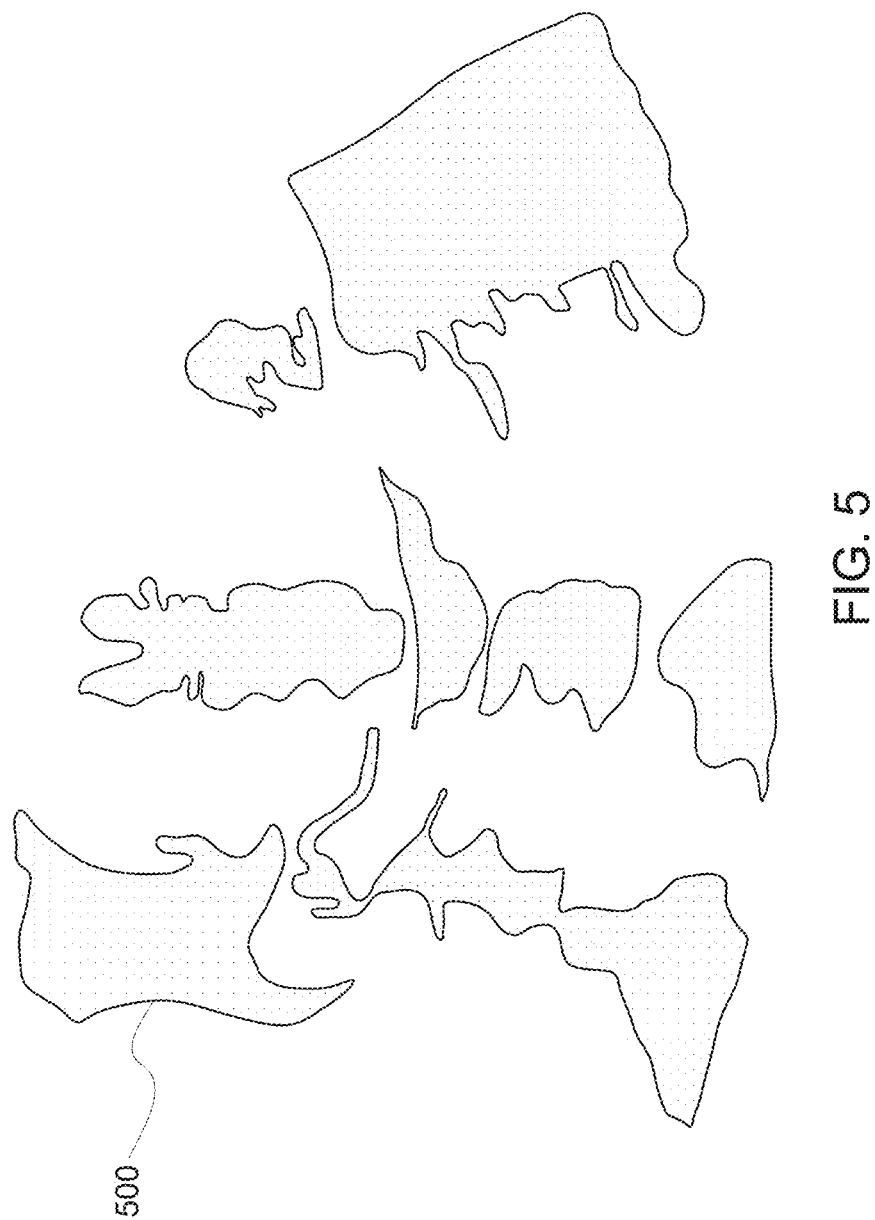
FIG. 5 is a representation of a mask in accordance with an embodiment.

The processor 116 may identify a region including one or more subregions with intensities that are less than the intensity threshold. The processor 116 may, according to an embodiment, apply a size filter to the portion of the image identified based on the intensity threshold. For example, small blood vessels and other structures may result in small regions with very low intensity that are not shadow artifacts. The processor 116 may compare the size of each of the subregions to threshold size. The processor 116 may, for instance, only include the subregions that are larger than the threshold size. This way, small low-intensity regions that accurately map to anatomical data are excluded from the mask. Next, the processor 116 generates a mask based on the identified shadow region 402 shown in FIG. 4. FIG. 4 shows the image 400 with a mask 500 superimposed on the image. FIG. 5 shows the mask 500 without the image 300. The mask 500 defines the regions that are included in the shadow region 402.

According to another embodiment, the processor 116 may be configured to generate a mask including the non-shadow region 404 of the image 400 instead of the shadow region 402. The non-shadow region 404 may be identified by identifying the portion of the image 400 with intensities above a threshold. According to an embodiment, the mask of the non-shadow region 404 may be the inverse of the mask of the shadow region 402.

According to other embodiments, the processor 116 may be configured to identify the shadow region 402 based on the ultrasound data using artificial intelligence techniques. For example, a neural network may be trained with curated images where the shadow region has been labeled. Based on the curated training images, the neural network may be configured to identify the shadow region in either the first image generated based on the first ultrasound data or the second image based on the second ultrasound data.

Figure 6:
FIG. 6 is an enhanced image in accordance with an embodiment.

Next, at step 318, the processor 116 generates an enhanced image. FIG. 6 shows an enhanced image 600 according to an exemplary embodiment. The enhanced image 600 includes an enhanced shadow region 602 and a non-shadow region 604. The enhanced shadow region 602 corresponds to the shadow region 402 in the mask 500. The processor 116 may, for instance, use the mask in order to define the region or area that is included in the enhanced shadow region 602. For example, FIG. 4 shows the mask 500 overlaid on top of the image 400. The mask 500 defines the shadow region 402 with respect to the anatomy represented in the image 400. The enhanced shadow region 602 in the enhanced image 600 is the same portions of the image, and therefore includes the same portions of the patient's anatomy, that were defined by the mask 500 with respect to the first image 400.

The method 300 requires specifically entering a shadow reduction mode in order to provide greater penetration. The method 300 requires specifically transmitting second ultrasound energy with a second transmit pattern that is configured to have greater penetration than first ultrasound energy transmitted with a first transmit pattern while in a non-shadow-reduction mode. The method 300 has the advantage of entering a specific shadow reduction mode and using a transmit pattern specifically tuned to provide greater penetration. Entering a specific shadow reduction mode and transmitting the second ultrasound energy with a second transmit pattern while in the shadow reduction mode allows for the use of a transmit pattern that would not be optimized for normal imaging in a non-shadow-reduction mode. For example, the second transmit pattern, used in the shadow reduction mode, may be tuned in a way that would emphasizes penetration at the expense of image quality or involve other trade-offs that would not be desirable to make when imaging anatomical regions without shadow regions. It would not be desirable to use a transmit pattern that emphasized penetration at the expense of image quality for imaging anatomical regions for imaging in a normal (non-shadow-reduction) mode. The method 300 therefore allows for a second transmit pattern with increased penetration, which is useful for generating an enhanced image in a shadow reduction mode with an enhanced shadow region.

Figure 7:
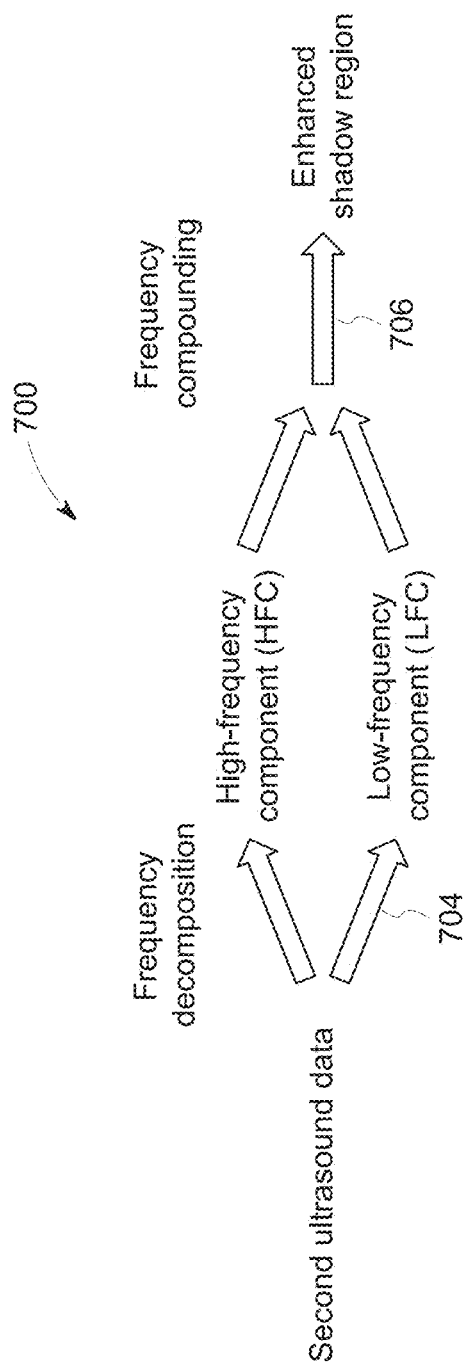
FIG. 7 is flow diagram in accordance with an embodiment.

According to an embodiment, the processor 116 may generate both the non-shadow region 604 and the enhanced shadow region 602 based on the second ultrasound data. FIG. 7 is a high level flow diagram 700 illustrating a technique that the processor 116 may use to generate the enhanced shadow region 602 in the enhanced image 600.

Diagram 700 shows how frequency compounding may be used to generate the enhanced shadow region according to an exemplary embodiment. In the diagram 700, at step 704, the second ultrasound data is processed into a high-frequency component (HFC) and a low-frequency component (LFC). According to an embodiment, the processor 116 may decompose the second ultrasound data into the HFC and the LFC using Fourier analysis. At step 706, the processor 116 performs frequency compounding using the HFC and the LFC in order to generate the enhanced shadow region. The processor 116 may perform a similar workflow for the non-shadow region in the enhanced image. For example, the processor 116 may recombine the HFC and the LFC of the second ultrasound data with a different weighting in order to generate the non-shadow region in the enhanced image 600. For example, as discussed above, it may be desirable to use lower frequency ultrasound data to generate the enhanced shadow region in the enhanced image 600. The processor 116 may be configured to deemphasize the HFC in the enhanced shadow region compared to the non-shadow region. For example, according to an embodiment, the intensity of the HFC in the enhanced shadow region may be reduced by at least 5 dB in the enhanced shadow region compared to the non-shadow region. According to another embodiment, the intensity of the HFC in the enhanced shadow region may be reduced by at least 10 dB. The enhanced image 600 therefore uses frequency compounded data with a greater relative contribution from the LFC in the enhanced shadow region compared to the non-shadow region. According to other embodiments, the processor 116 may reduce the amount of the LFC used in the generation of the non-shadow regions in the enhanced image 600 either in addition to deemphasizing the high-frequency component in the enhanced shadow region or in place of deemphasizing the high-frequency component in the enhanced shadow region. While FIG. 7 shows decomposing the ultrasound data into a HFC and a LFC, in other embodiments, the processor 116 may be configured to decompose the ultrasound data into two or more HFCs and/or two or more LFCs using Fourier processing.

Both the enhanced shadow region 602 and the non-shadow region 604 in the enhanced image 600 may be generated based on the second ultrasound data using frequency compounding as described above, or the non-shadow region 604 may be generated using frequency compounding based on the first ultrasound data while the enhanced shadow region 602 is generated using frequency compounding based on the second ultrasound data.

According to another embodiment, the enhanced processor 116 may generate the enhanced shadow region 602 based on ultrasound data with a lower center frequency than the ultrasound data used to generate the non-shadow region 604 in the enhanced image 600. For example, according to an embodiment where the second transmit pattern is at a lower center frequency than the first transmit pattern, the processor 116 may use non-frequency-compounded ultrasound data to generate one or both of the enhanced shadow region 602 and the non-shadow region 604 in the enhanced image 600. According to an embodiment, the enhanced shadow region 602 may be generated using non-frequency-compounded data based on the second ultrasound image data and the non-shadow region 604 may be generated using non-frequency-compounded data based on the first ultrasound data.

According to another embodiment, the processor 116 may be configured to generate both the enhanced shadow region 602 and the non-shadow region 604 based on the second ultrasound data. The processor 116 may, for instance, use the HFC of the second ultrasound data without the LFC to generate the non-shadow region 604, and the processor 116 may use the LFC without the HFC to generate the enhanced shadow region 602 in the enhanced image 600.

According to an embodiment, the processor 116 may be configured to generate both the enhanced shadow region 602 and the non-shadow region 604 based on the second ultrasound data. The processor 116 may, for instance, use the HFC of the second ultrasound data without the LFC to generate the non-shadow region 604, and the processor 116 may use frequency compounding to combine both the HFC and the LFC of the second ultrasound data to generate the enhanced shadow region 602. According to an embodiment, the processor 116 may emphasis the LFC of the second ultrasound data more strongly than the HFC when frequency compounding the second ultrasound data for the enhanced shadow region in order to have greater penetration.

According to another embodiment, the second transmit pattern used to acquire the second ultrasound data may be a coded excitation pattern that is tuned to give greater penetration than the first transmit pattern. According to this embodiment, the processor 116 may be configured to generate the enhanced shadow region 602 in the enhanced image 600 using the second ultrasound data and to generate the non-shadow region 604 based on the first ultrasound data acquired using the first transmit pattern.

According to another embodiment, the second transmit pattern used to acquire the second ultrasound data may be a pulse inversion technique that is tuned to give greater penetration than the first transmit pattern. According to this embodiment, the processor 116 may be configured to generate the enhanced shadow region 602 in the enhanced image using the second ultrasound data and to generate the non-shadow region 604 based on the first transmit pattern.

The processor 116 may be configured to combine one or more of the techniques described hereinabove. Additionally, the processor 116 may use different techniques for generating the enhanced shadow region 602 and the non-shadow region 604. For example, the processor 116 may generate the enhanced shadow region 602 of the enhanced image 602 using a first technique. The first technique may, for instance, be a frequency compounding technique, and it may include a coded excitation technique or a pulse inversion technique. And, the processor 116 may generate the non-shadow region 604 of the enhanced image 600 using a second technique that is different than the first technique. The second technique may be a frequency compounding technique and it may include a coded excitation technique or a pulse inversion technique. As discussed hereinabove, regardless of the technique used, the second transmit pattern used to acquire the first ultrasound data is always configured to have greater penetration than the first transmit pattern used to acquire the first ultrasound data. And, the second ultrasound data, acquired with the second transmit pattern, is used to generate the enhanced shadow region 602 in the enhanced image 600.

According to various embodiments, the processor 116 may use a transition zone to allow for a visually smoother transition between the enhanced shadow region 602 and the non-shadow region 604 when generating the enhanced image 600. For example, the transition zone may be within the area defined by the mask 500, adjacent to the edges of the area defined by the mask 500 or the transition zone may be positioned both within the area defined by the mask 500 and within the region adjacent to the edges of the area defined by the mask 500. The processor 116 may be configured to apply a function to smoothly blend the image in the transition zone from the enhanced shadow region 602 to the non-shadow region 604. For example, according to an embodiment where the enhanced image is generated by controlling the amount of HFC and LFC used for the enhanced shadow region 602 and the non-shadow region 604, the processor 116 may adjust the relative contributions of the HFC and the LFC in the transition zone to create a visually smoother transition between the enhanced shadow region 602 and the non-shadow region 604. The processor 116 may be configured to adjust the image within the transition zone according to other techniques according to other embodiments. The function used in the transition zone may be a linear function or it may be any other type of function. The length of the transition zone may be adjusted based on the parameters used for the enhanced image 600. For example, the width of the transition zone may vary based on the frequency used for the acquisition of the enhanced image 600. According to an embodiment, an enhanced image acquired with a lower frequency may have a longer transition zone than an enhanced image acquired with a higher frequency. According to an exemplary embodiment, the transition zone may be a region that is 4 mm wide. The 4 mm wide transition zone may be entirely within the area defined by the mask 500, the 4 mm wide transition zone may be adjacent to and outside of the area defined by the mask 500, or the 4 mm wide transition zone may be split between the area defined by the mask and the region outside of the area defined by the mask 500. For example, the transition zone may be positioned so 2 mm is within the area defined by the mask 500 and 2 mm is adjacent to the area defined by the mask 500. While an example was described using a 4 mm wide transition zone, it should be appreciated that transition zones of various widths may be used according to different embodiments. Additionally, the processor 116 may be configured to apply transition zones that are different widths in the lateral and azimuthal directions.

Using the second ultrasound data, acquired with a second transmit pattern configured to have greater penetration than the first transmit pattern, and using the second ultrasound to generate an enhanced shadow region in an enhanced image allows for the generation of an enhanced image with a reduction in shadow artifacts due to the increased penetration of the second transmit pattern. This results in higher overall image quality and allows for more accurate measurement and clinical diagnoses.

Referring to the method 300, at step 320, the processor 116 displays the enhanced image on the display device 118.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for ultrasound imaging comprising:
transmitting first ultrasound energy from an ultrasound probe with a first transmit pattern having a first center frequency;
receiving first ultrasound data based on the first ultrasound energy;
generating a first image based on the first ultrasound data;
entering a shadow-reduction mode in response to a user input after said generating the first image and performing the following steps while in the shadow-reduction mode:
transmitting second ultrasound energy from the ultrasound probe with a second transmit pattern having a second center frequency, wherein the second center frequency is lower than the first center frequency;
receiving second ultrasound data based on the second ultrasound energy;
decomposing the second ultrasound data into a high-frequency component and a low-frequency component;
identifying a shadow region based on the second ultrasound data before the second ultrasound data has been scan-converted;
generating a mask based on the shadow region, wherein said generating the mask is performed before the second ultrasound data has been scan-converted, and wherein the mask identifies a shadow region or a non-shadow region;
generating an enhanced image based on the second ultrasound data and the mask, wherein said generating the enhanced image comprises emphasizing the high-frequency component of the second ultrasound data corresponding to the non-shadow region and emphasizing the low-frequency component of the second ultrasound data in an enhanced shadow region corresponding to the shadow region;
scan-converting the enhanced image; and
displaying the enhanced image on a display device after the enhanced image has been scan-converted.

2. The method of claim 1, wherein the second transmit pattern is a coded excitation technique.

3. The method of claim 1, wherein the second transmit pattern comprises a pulse inversion technique.

4. The method of claim 1, wherein said generating the mask comprises using an artificial intelligence technique to generate the mask.

5. The method of claim 1, wherein said generating the mask comprises identifying a portion of the first image with an intensity below an intensity threshold.

6. An ultrasound imaging system comprising:
a display device;
an ultrasound probe; and
a processor in electronic communication with both the display device and the ultrasound probe, wherein the processor is configured to:
control the ultrasound probe to transmit first ultrasound energy with a first transmit pattern having a first center frequency;
receive first ultrasound data based on the first ultrasound energy;
generate a first image based on the first ultrasound data;
enter a shadow-reduction mode in response to a user input after generating the first image and perform the following steps while in the shadow-reduction mode:
control the ultrasound probe to transmit second ultrasound energy with a second transmit pattern having a second center frequency, wherein the second center frequency is lower than the first center frequency;
receive second ultrasound data based on the second ultrasound energy;
decompose the second ultrasound data into a high-frequency component and a low-frequency component;
identify a shadow region based on the second ultrasound data before the second ultrasound data has been scan-converted;
generate a mask based on the shadow region before the second ultrasound data has been scan-converted, wherein the mask identifies a shadow region or a non-shadow region;
generate an enhanced image based on the second ultrasound data and the mask, wherein the processor is configured to generate the enhanced image by emphasizing the high-frequency component of the second ultrasound data corresponding to the non-shadow region and emphasizing the low-frequency component of the second ultrasound data in an enhanced shadow region corresponding to the shadow region;
scan-convert the enhanced image; and
display the enhanced image on the display device.

7. The ultrasound imaging system of claim 6, wherein the processor is configured to implement an artificial intelligence algorithm to identify the shadow region in order to generate the mask.

8. The method of claim 1, wherein the mask identifies the shadow region.

9. The method of claim 1, wherein the mask identifies the non-shadow region.

10. The method of claim 1, further comprising applying a function to smoothly blend the enhanced image from the enhanced shadow region to the non-shadow region.

11. The ultrasound imaging system of claim 6, wherein the mask identifies the shadow region.

12. The ultrasound imaging system of claim 6, wherein the mask identifies the non-shadow region.

13. The ultrasound imaging system of claim 6, wherein the processor is configured to apply a function to smoothly blend the enhanced image from the enhanced shadow region to the non-shadow region.

* * * * *